(12) United States Patent
Tah et al.

(10) Patent No.: US 9,855,066 B2
(45) Date of Patent: Jan. 2, 2018

(54) RETRIEVAL DEVICE AND RELATED METHODS OF USE

(71) Applicant: Boston Scientific Scimed, Inc., Maple Grove, MN (US)

(72) Inventors: Richard C. Tah, Framingham, MA (US); Ronald Ciulla, Westford, MA (US); Michael F. Weiser, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 179 days.

(21) Appl. No.: 14/204,984

(22) Filed: Mar. 11, 2014

(65) Prior Publication Data
US 2014/0276913 A1    Sep. 18, 2014

Related U.S. Application Data

(60) Provisional application No. 61/778,022, filed on Mar. 12, 2013.

(51) Int. Cl.
*A61B 17/26* (2006.01)
*A61B 17/221* (2006.01)
(Continued)

(52) U.S. Cl.
CPC ...... *A61B 17/221* (2013.01); *A61B 17/22031* (2013.01); *A61B 18/082* (2013.01);
(Continued)

(58) Field of Classification Search
CPC ............ A61B 17/221; A61B 17/22031; A61B 2017/00274; A61B 18/082;
(Continued)

(56) References Cited

U.S. PATENT DOCUMENTS 4,950,278 A    8/1990    Sachse et al.
5,025,778 A    6/1991    Silverstein et al.
(Continued)

FOREIGN PATENT DOCUMENTS

GB        2479582 A      10/2011
WO     WO 97/25917       7/1997
(Continued)

OTHER PUBLICATIONS

International Search Report and Written Opinion for counterpart PCT Application No. PCT/US2014/023615 dated Jun. 17, 2014 (14 pages).

*Primary Examiner* — Richard Louis
(74) *Attorney, Agent, or Firm* — Bookoff McAndrews, PLLC

(57) ABSTRACT

Embodiments of the present disclosure provide a device for extracting and/or morcellating tissue or other unwanted material from within a patient's body. In one embodiment, a medical device may include an elongate member including a proximal end, a distal end, and a lumen extending therebetween. The medical device may also include an expandable member disposed at the distal end, wherein an interior of the expandable member is in fluid communication with the lumen in the elongate member, wherein the expandable member includes a plurality of conducting elements extending from and disposed circumferentially about the elongate member, wherein at least two of the plurality of conducting elements are joined together by a material extending therebetween.

20 Claims, 7 Drawing Sheets

(51) Int. Cl.
*A61B 17/22* (2006.01)
*A61B 18/14* (2006.01)
*A61B 18/00* (2006.01)
*A61B 18/08* (2006.01)
*A61B 17/00* (2006.01)

(52) U.S. Cl.
CPC ..... *A61B 18/14* (2013.01); *A61B 2017/00274* (2013.01); *A61B 2017/2215* (2013.01); *A61B 2018/00267* (2013.01); *A61B 2218/007* (2013.01)

(58) Field of Classification Search
CPC .. A61B 2018/00267; A61B 2017/2215; A61B 18/14; A61B 2218/007
See application file for complete search history.

(56) References Cited

U.S. PATENT DOCUMENTS

| | | | |
|---|---|---|---|
| 5,549,626 A | 8/1996 | Miller et al. | |
| 6,123,701 A | 9/2000 | Nezhat | |
| 6,174,307 B1 | 1/2001 | Daniel et al. | |
| 6,221,007 B1 | 4/2001 | Green | |
| 6,440,061 B1 | 8/2002 | Wenner et al. | |
| 7,267,674 B2 | 9/2007 | Brucker et al. | |
| 7,357,801 B2 | 4/2008 | Burbank et al. | |
| 7,491,165 B2 | 2/2009 | Kogasaka et al. | |
| 7,578,786 B2 | 8/2009 | Boulais et al. | |
| 7,794,409 B2 | 9/2010 | Damarati | |
| 7,878,983 B2 | 2/2011 | Karpiel | |
| 7,922,650 B2 | 4/2011 | McWeeney et al. | |
| 8,140,141 B2 | 3/2012 | McGreevy et al. | |
| 8,152,737 B2 | 4/2012 | Burbank et al. | |
| 8,182,415 B2 | 5/2012 | Larkin et al. | |
| 8,221,403 B2 | 7/2012 | Sharkey et al. | |
| 8,235,887 B2 | 8/2012 | Bayer et al. | |
| 8,277,392 B2 | 10/2012 | Karpiel | |
| 8,279,079 B2 | 10/2012 | Bergman et al. | |
| 8,289,391 B2 | 10/2012 | Kiyohara et al. | |
| 2001/0039420 A1 | 11/2001 | Burbank et al. | |
| 2002/0173815 A1* | 11/2002 | Hogendijk et al. | 606/194 |
| 2003/0032953 A1 | 2/2003 | VanDusseldorp et al. | |
| 2004/0204709 A1 | 10/2004 | Burbank et al. | |
| 2005/0182433 A1* | 8/2005 | Nady | A61B 17/22 606/170 |
| 2005/0228403 A1* | 10/2005 | Ho | A61B 10/0266 606/113 |
| 2005/0272975 A1* | 12/2005 | McWeeney | A61B 1/00071 600/113 |
| 2006/0074410 A1* | 4/2006 | Malecki | A61B 18/1492 606/32 |
| 2007/0123852 A1* | 5/2007 | Deem | A61B 18/1492 606/45 |
| 2007/0225702 A1 | 9/2007 | Kaouk | |
| 2008/0077045 A1 | 3/2008 | Burbank et al. | |
| 2008/0091215 A1* | 4/2008 | Saleh | 606/113 |
| 2008/0097424 A1 | 4/2008 | Wizeman et al. | |
| 2008/0119869 A1* | 5/2008 | Teague et al. | 606/127 |
| 2008/0221437 A1 | 9/2008 | Agro et al. | |
| 2010/0152765 A1* | 6/2010 | Haley | A61F 2/01 606/200 |

FOREIGN PATENT DOCUMENTS

| | | | |
|---|---|---|---|
| WO | WO 2008/028149 A2 | 3/2008 | |
| WO | WO 2012162437 A1 * | 11/2012 | A61F 2/06 |

* cited by examiner

RETRIEVAL DEVICE AND RELATED METHODS OF USE

This application claims the benefit of U.S. Provisional Application No. 61/778,022, filed Mar. 12, 2013, the disclosure of which is incorporated herein by reference in its entirety.

FIELD

Embodiments of the present disclosure relate generally to devices suitable for use in medical procedures. In particular, embodiments of the present disclosure relate to apparatuses and methods for removing tissues, stones, or otherwise undesired materials from within a patient's body.

BACKGROUND

Bladder obstruction, arising from enlargement of the prostate gland in males, is one of the most common disorders in urology. The prostate gland lies under the bladder and surrounds the passageway known as the prostatic urethra, which transfers fluids from the bladder to the sphincter and ultimately outside the body through the rest of the urethra. An enlarged prostate may constrict the prostatic urethra leading to a condition known as benign prostatic hyperplasia ("BPH"). BPH may cause a variety of obstructive symptoms, including urinary hesitancy, decreased size and force of the urinary stream, bladder calculi, and in extreme cases, complete urinary retention, which may lead to renal failure.

To overcome these and other problems, the enlarged prostate may be surgically removed after severing the gland from the body. One BPH treatment, referred to as enucleation of the prostate, may employ a minimally invasive device, such as a cystoscope or a nephroscope, that may include one or more channels to insert devices such as an incising device, a morcellating device, and/or an extraction device. The incising device, which may include, e.g., a Holmium laser or another mechanical cutting device, may carve out or cut the prostate lobes. The severed prostate lobes/tissues may generally be large, and be pushed or fall into the bladder. Therefore, a morcellating device may be used to fragment the larger tissue pieces to facilitate easier removal of the excised tissue.

Typically, morcellation of a tissue may be accomplished with a mechanical morcellator. A mechanical morcellator may include blades (e.g., attached to a handle) to morcellate the tissue into smaller pieces. A vacuum pump or other source of suction may be connected to the morcellator to provide suction through the blades for suctioning the morcellated tissue pieces out of the bladder. The process may be conducted with saline circulation through the bladder to prevent the bladder walls from collapsing into the morcellator blades.

The morcellation process, as described above, has the possibility of injury to the bladder walls in case the bladder walls come in contact with the morcellator blades. Further, the process of morcellation may be time consuming.

SUMMARY

Embodiments of the present disclosure provide a device for extracting and/or morcellating tissue or other unwanted material from within a patient's body. In one embodiment, a medical device may include an elongate member including a proximal end, a distal end, and a lumen extending therebetween. The medical device may also include an expandable member disposed at the distal end, wherein an interior of the expandable member is in fluid communication with the lumen in the elongate member, wherein the expandable member includes a plurality of conducting elements extending from and disposed circumferentially about the elongate member, wherein at least two of the plurality of conducting elements are joined together by a material extending therebetween.

In another embodiment, a tissue retrieval system may include an elongate introduction sheath having a proximal end, a distal end, and a plurality of channels extending therebetween, wherein one of the plurality of channels includes a cross-sectional dimension larger than a cross-sectional dimension of a remainder of the plurality of channels, and wherein at least one of the remainder of the plurality of channels includes one of an illumination device and an imaging device. The tissue retrieval system may also include a morcellating device configured to be disposed within the one of the plurality of channels. In one embodiment, the tissue morcellating device may include an elongate member including a proximal end, a distal end, and a lumen extending therebetween. The tissue morcellating device also may include a basket defining a selectively closable opening disposed at the distal end of the elongate member, wherein an interior of the basket is in fluid communication with the lumen in the elongate member and, wherein the basket further includes a plurality of conducting elements.

In a further embodiment, a method of retrieving unwanted material from within a patient's body may include advancing a tissue retrieval device to a location adjacent the unwanted material within the patient's body. The tissue retrieval device may include an expandable basket defining a distal opening, wherein the basket includes a plurality of conducting elements. The method also may include entrapping the unwanted material within the basket, energizing the plurality of conducting elements, collapsing the expandable basket about the unwanted material so that the energized plurality of conducting elements cut the unwanted material into multiple pieces, and withdrawing the multiple pieces of unwanted material from within the patient's body.

It is to be understood that both the foregoing general description and the following detailed description are exemplary and explanatory only and are not restrictive of the embodiments disclosed herein.

BRIEF DESCRIPTION OF THE DRAWINGS

The accompanying drawings, which are incorporated in and constitute a part of this specification, illustrate embodiments of the present disclosure and together with the description, serve to explain the principles of the embodiments disclosed herein.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts.

Overview

The present disclosure relates generally to a device to facilitate morcellation and/or removal of undesirable material from a body. The device may excise and/or morcellate an undesirable mass into smaller pieces, illuminate the surgical site, provide a means to view the surgical site, and provide a passageway for extracting pieces from the body. To this end, the device includes an elongate tube having one or more lumens or working channels. It should be understood that the device may use one or more medical devices to accomplish a morcellation and/or tissue removal process. In general, the device may include, without limitation, a visualization or imaging device, a light source, a morcellating device, a suction device such as, e.g., a vacuum pump, and/or other known devices. These devices may be integrally formed with the device and/or one or more of these devices may be removably disposed within one or more channels of the device.

Embodiments of the present disclosure employ a single elongate tube having one or more lumens for accommodating all the required medical devices, including morcellating and suction devices. The size and the number of lumens may be modified to suit the requirements of a desired application or procedure, as desired. For example, the lumen through which the morcellating device that is capable of morcellating and optionally, extracting a tissue, may have the largest cross-sectional diameter relative to any other lumens or passageways. In an embodiment, the disclosed morcellating device may employ RF morcellation. Using the morcellation process of the present disclosure, the possibility of injury to the surrounding tissues, e.g., bladder walls may be minimized or eliminated.

Although exemplary embodiments of the present disclosure are described with reference to a prostatectomy procedure, it will be appreciated that aspects of the present disclosure have wide and varying applications. Embodiments of the present disclosure can be used for a variety of therapeutic procedures, including ureteroscopy, hysteroscopy, and cystoscopy. The disclosed devices and techniques may be suitable to morcellate and optionally remove any body part or otherwise undesired material from within a body. For example, the device may be utilized to remove tissue or bladder stones, or even biliary and kidney stones. Accordingly, the following descriptions and illustrations should be considered illustrative in nature, not limiting the scope of the claimed invention.

Exemplary Embodiments

Figure 1:
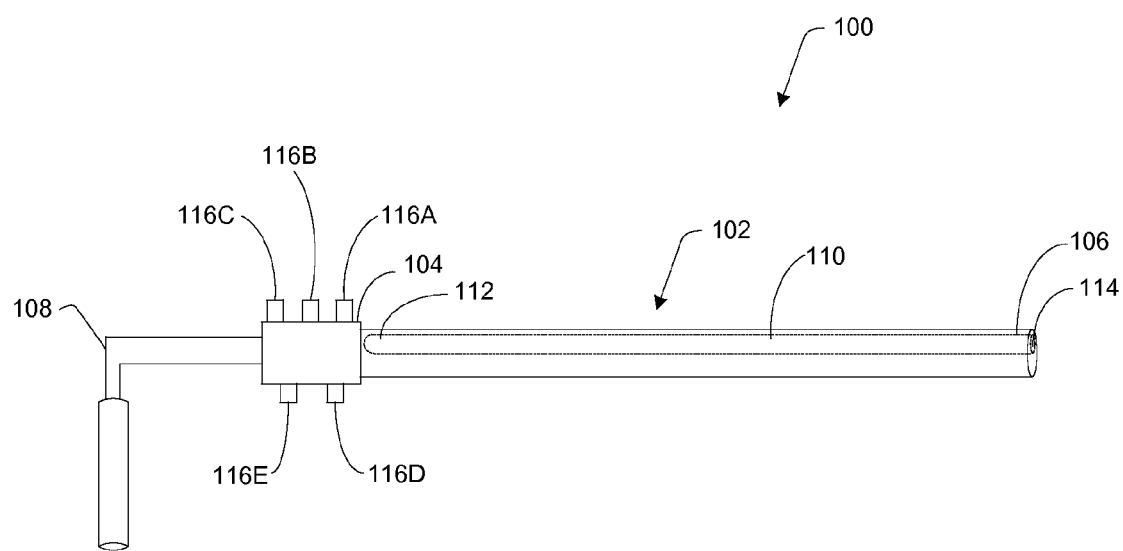
FIG. 1 is a schematic view of an exemplary insertion device, according to an embodiment of the present disclosure.

FIG. 1 provides a schematic view of an embodiment of an insertion device 100 for resecting and/or retrieving undesired material from within a body through, e.g., an incision or a natural body opening. Device 100 may include an elongate introduction sheath or tube 102 having a proximal end 104 and a distal end 106, and a handle 108 coupled to the proximal end 104 of tube 102. The tube 102 may include one or more channels 110 having proximal and distal end openings 112, 114, respectively, to receive, e.g., one or more medical devices. The channels 110 may be used for, among other things, providing irrigation, light, morcellation, suction, and/or insufflations. It is understood that "proximal" and "distal" refers to positions or directions nearer to or farther from the user, respectively.

Tube 102 may be advanced into a natural orifice and/or an incision, as desired. Tube 102 may be substantially hollow, with a cross sectional configuration adapted to be received in a desired body lumen. In the illustrated embodiment, e.g., tube 102 may include a generally circular cross sectional configuration. Further, the tube 102 may have a uniform diameter or may taper at its distal end 106 to allow convenient insertion into the body. In an alternate embodiment, the cross sectional dimensions and/or configurations of tube 102 may vary along its length, as desired. For example, a proximal portion of tube 102 may include a hexagonal cross sectional configuration while a distal portion of tube 102 includes a rectangular cross sectional configuration, based on the intended use and application. In addition, tube 102 may include transparent or translucent portions, allowing an operator to view devices held within tube 102. Additionally, a tube 102 having transparent portions may facilitate visualizing portions of a patient's body through a wall of tube 102. Although tube 102 extends distally from handle 108 in FIG. 1, it may be configured for use without the handle 108 during a portion or all of a surgical procedure.

Depending upon the particular implementation and intended use, the length of tube 102 may vary. For example, the length of tube 102 may be relatively longer for procedures within longer cavities or deeper organs, such as the bowel or intestine. Similarly, depending upon the particular implementation and intended use, the tube 102 can be rigid along its entire length, flexible along a portion of its length, or configured for flexure or steering at only certain specified locations.

The proximal end 104 of tube 102 can be coupled to handle 108 for gripping by an operator such as a surgeon, while the distal end 106 remains open to allow medical devices to extend out from tube 102. The handle 108 can be attached to tube 102 by any suitable means, including, for example, welding, use of an adhesive, or integrally formed with tube 102. In some embodiments, the handle 108 may be selectively attached and detached from tube 102 as desired.

Tube 102 may be adapted to receive multiple medical devices therein. To this end, proximal end 104 of tube 102 may include multiple ports 116A, 116B, 116C, 116D, and 116E, collectively referred to as ports 116. Each of ports 116 may connect to a channel of the tube and a medical device may be advanced into the port 116 for extending from the distal end 106 of the tube 102 via the corresponding channel. Multiple ports 116 may connect to a single channel, such as, e.g., channel 110, within tube 102. Medical devices that may be inserted into one of the ports include, without limitation, medical, auxiliary or accessory devices and the morcellating device of the present disclosure. For example, port 116A may be coupled to a visualization device such as a camera; port 116B may be coupled to a light source; ports 116C and 116D may be coupled to a laser system and a morcellating device, e.g., the morcellating device 400A or 400B (shown in FIGS. 4A-4B respectively); and port 116E may be attached to a suction device or an irrigation source. The laser system may introduce a laser fiber into a channel for resecting or cutting undesired mass from a tissue or gland.

In addition to a laser fiber, other suitable devices may be used in accordance with the principles of the present disclosure. Such devices may include, e.g., a lithotripter or other sources of energy including high intensity focused ultrasound and radiofrequency.

Alternately, the proximal end 104 of the tube 102 may include connections to which the medical or other devices may be coupled. For example, an electrosurgical or RF generator may be coupled to a connection for providing the energy needed to morcellate or otherwise reduce tissue pieces. In yet another embodiment, ports as well as connections may be provided at the proximal end 104 of tube 102. In general, the number of ports/connections may correspond to the number of channels 110 within the tube 102. Alternatively, the number of ports/connections may be greater or less than the number of channels 110. That is, e.g., two ports 116 may be operably coupled to a single channel 110.

"Port" may refer to a proximal end opening of a channel 110 or it may be an additional opening attaching the tube's proximal end 104 to channel's proximal end opening 112. Alternatively, proximal end 104 of tube 102 may be opened to insert medical devices directly into one or more of the channels 110.

Tube 102 may be made of any suitable material that is compatible with living tissue or a living system. That is, the tube should be non-toxic or non-injurious, and it should not cause immunological reaction or rejection. Suitable materials may include, e.g., nitinol, ePTFE, fabric, and suitable nickel and titanium alloys.

Tube 102 may be flexible or adapted for flexible steering within bodily lumens, as understood in the art. In such implementations, tube 102 may be a flexible sheath, surrounding channels 110, made of fiber or wires that may be woven or braided together. Suitable flexible materials may include synthetic plastics, fiber, or polymers.

In addition, tube 102 may include known steering mechanisms to allow tube 102 to be selectively maneuvered. An exemplary steering mechanism may include, e.g., a pull wire extending through the tube 102 and controlled by the handle 108. Alternatively, tube 102 may be rigid or semi-rigid and be made of materials, such as, stainless steel, including shape memory alloys such as nitinol. Further, although not shown, tube 102 may be made of a plurality of articulating segments coupled together and movable relative to one another.

In an alternative embodiment, portions of tube 102 may be expandable (e.g., self-expandable) or compressible. For example, a cross-section of tube 102 may be compressed to reduce the tube's overall diameter, allowing insertion into relatively smaller body lumens, such as, those in a patient's urethra. In the expanded configuration, tube 102 may expand in the radial direction. The expanded state may allow passage of one or more medical devices, including, e.g., morcellating devices 400A or 400B (shown in FIGS. 4A-4B, respectively). Expansion and/or compression of tube 102 may be achieved by incorporating various known expansion mechanisms including a spring, basket, coil, or inflatable structure within the tube 102. In an embodiment, tube 102 may be made of shape memory material such as Nitinol that changes shape on exposure to a trigger (e.g., body chemistry or temperature) or removal of a constraining force.

Tube 102 may include multiple channels 110 which may receive two or more devices, independently or simultaneously. Each channel 110 may be configured to receive at least one medical device through the corresponding port 116(*a-e*). In addition, one or more of channels 110 may be configured to facilitate irrigation, suction, and/or insufflation. In general, channels 110 may be hollow elongate structures extending from proximal end 104 to distal end 106 of tube 102. One or more of channels 110 may include suitable geometric features (not shown) configured to, e.g., guide and/or center a medical device disposed therein.

Figure 2:
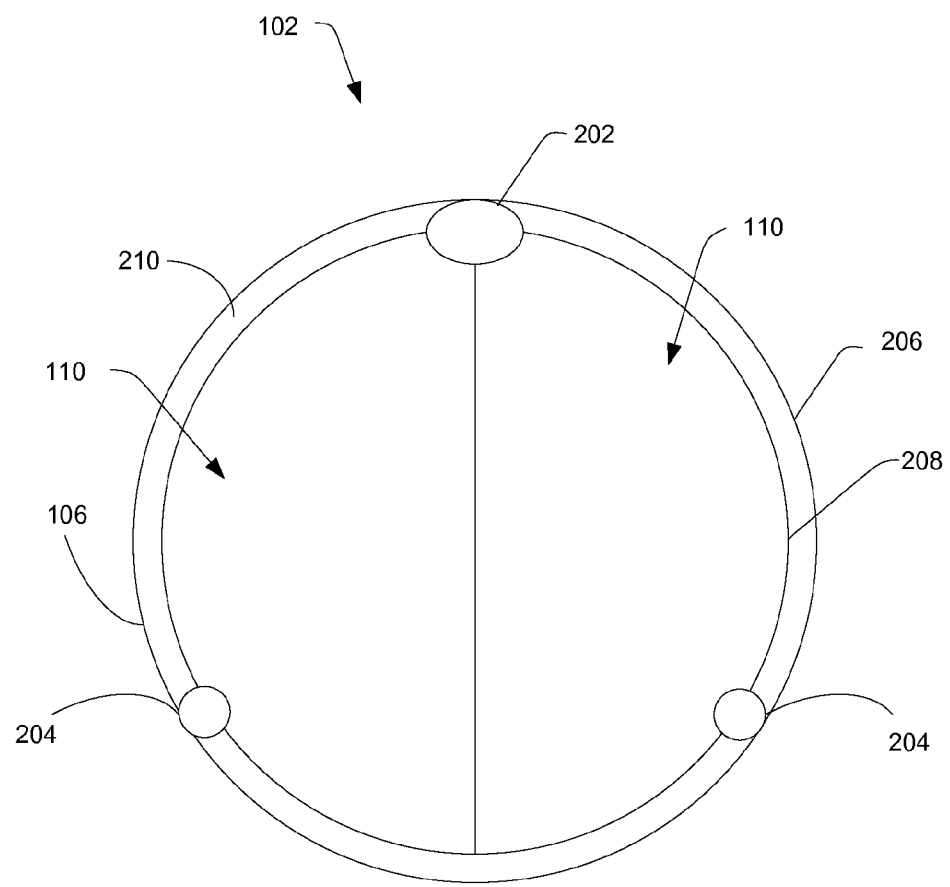
FIG. 2 illustrates an exemplary end view of one embodiment of the insertion device, in accordance with the present disclosure.

FIG. 2 illustrates a distal end view of the distal end 106 of an exemplary embodiment of tube 102, depicting channels 110 through which devices for example, morcellating devices 400A or 400B may be inserted. As shown, this embodiment of tube 102 includes two semi-circular shaped working channels 110, and a camera 202 and light sources 204 (combination referred to as "visualization device", hereafter) disposed at the distal end 106 of the tube 102. In some embodiments, rather than the camera 202 and light sources 204, an eye piece may be provided.

In general, working channels 110 can be defined by elongate hollow lumens that extend between proximal end 104 and distal end 106 of tube 102. While two channels are illustrated, fewer channels or more channels may be contemplated. The number of channels and their configuration can be varied depending on the intended use of the system and the tools required during a procedure. For example, the tube 102 can include a single channel adapted to receive multiple tools. In such a situation, a central lumen of tube 102 may itself act as the working channel 110.

In addition, the distal end 106 of tube 102 may include an imaging device, such as, e.g., camera 202 and light sources 204 for assisting a surgeon during procedure. As shown, these imaging and visualization devices are mounted on the circumferential distal end surface of tube 102 such that the devices are at least partially embedded within the walls defining tube 102. In general, tube 102 may include an outer surface 206 and an inner surface 208, and a material thickness 210 extends between the outer and inner surfaces 206 and 208. A portion of one or more of the visualization devices may extend into the thickness 210 and the remaining portion may protrude into one or more working channels 110. This provides for wider working channels for, among other things, enabling bigger tissue or stone fragments to be removed.

Figure 3:
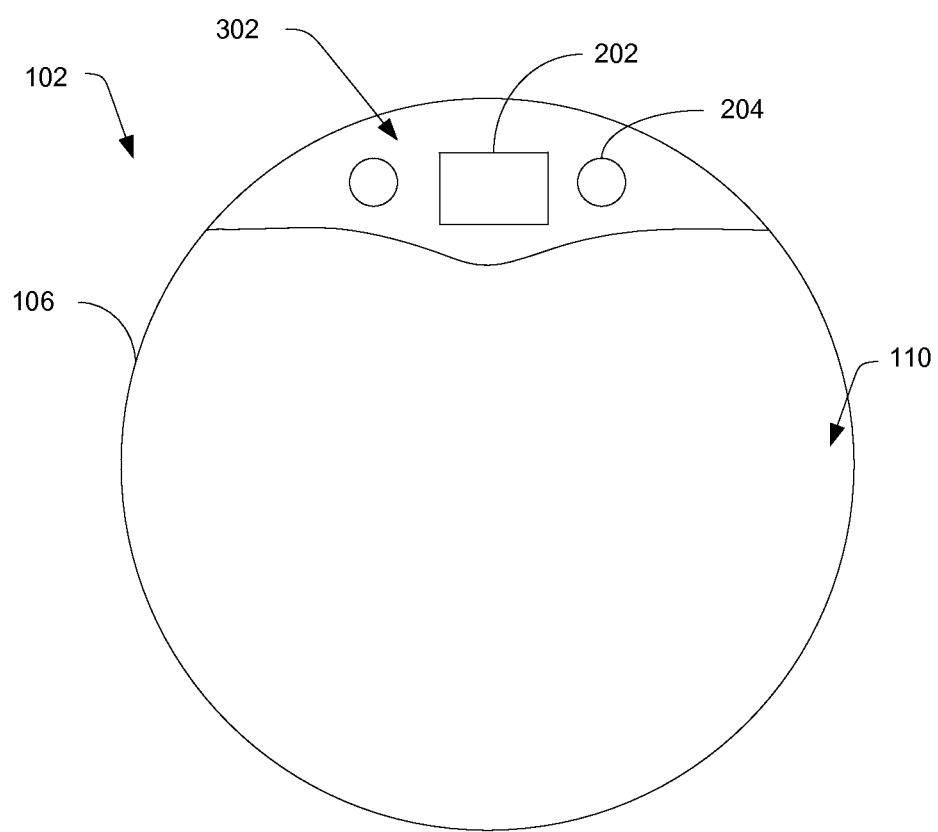
FIG. 3 illustrates an exemplary end view of a further embodiment of the insertion device, in accordance with the present disclosure.

FIG. 3 illustrates another exemplary embodiment of tube 102. As shown, camera 202 and light sources 204 may be integrated into a single visualization device 302, which may be removably attached to any suitable location along an inner surface of tube 102. Alternately, the visualization device 302 may be an eye piece. As noted, this visualization device 302 may be permanently or temporarily attached to the tube 102. For wireless connection, visualization device 302 may be a relatively small device connected to the distal end 106. For wired connections, however, visualization device 302 may also include an elongate portion running along the length of the tube 102. The present disclosure allows visualization devices to be detachably connected to tube 102 such that these devices may be retrieved, when not required, to increase the working channel area.

Owing to the visualization device 302 being at least partially embedded into the thickness of the tube 102, for example the working channel 110 may be made relatively larger. The enlarged working channel 110 may in turn be employed for introducing various devices and/or removing relatively larger fragments of tissue or stone from within a patient. In further embodiments, visualization device 302 may be configured to be disposed within an expandable pocket defined by a flexible, movable wall 304. Wall 304 may be configured to extend away from the walls of tube 102 when visualization device 302 is inserted into the pocket. When visualization device 302 is withdrawn, wall 304 may be configured to collapse, thereby increasing the volume of channel 110.

Figure 4A:
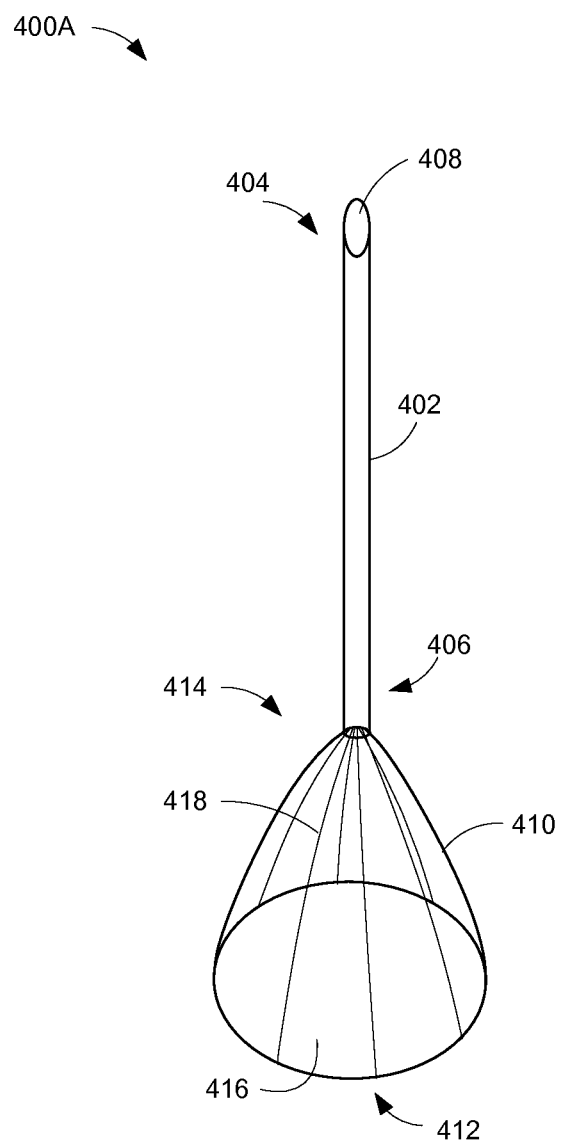
FIGS. 4A-4B illustrate exemplary embodiments of a morcellating device, in accordance with the present disclosure.

FIG. 4A illustrates a morcellating device 400A in accordance with a first embodiment of the present disclosure. The device 400A may include an elongate member 402 with a proximal end 404, distal end 406, and lumen 408 extending therebetween. The member 402 may be self-expandable or expanded and collapsed using an actuation mechanism. The member 402 may be introduced in the working channel 110 of the tube 102 in the collapsed configuration. In the expanded configuration, member 402 may expand in the radial direction and correspond to maximum available diameter of the working channel 110. The expanded state may allow, without limitation, retrieval of tissue fragments, insertion of medical devices like forceps, scissors, etc. therethrough. Expansion and/or compression of member 402 may be achieved by incorporating various known expansion mechanisms including springs, basket, or coil structure within the member 402. In an embodiment, member 402 may be made of shape memory material such as Nitinol that changes state on exposure to a trigger (e.g., body temperature or chemistry) or removal of a constraint.

The member 402 may be substantially hollow, with a cross sectional configuration adapted to be received in one of the working channels 110 of tube 102. In the illustrated embodiment in FIG. 4A, the member 402 is generally circular, with a generally circular hollow interior lumen. In some embodiments, the member 402 may have a uniform diameter or may taper at its distal end 406 to allow convenient insertion into the working channel 110. In an alternate embodiment, the cross sectional dimensions and/or configurations of member 402 may vary along its length, as desired. For example, a proximal portion of member 402 may include a hexagonal cross sectional configuration while a distal portion of member 402 may include a rectangular cross sectional configuration, based on the intended use and application. Alternately, the diameter of the member 402 may be selected such that it fits into the working channel 110 in which it is inserted.

Further, the member 402 may be transparent or translucent to enable an operator to track the movement of, e.g., tissue fragments therein. In various embodiments, the member 402 may be rigid or flexible. Exemplary rigid materials of which the member 402 can be made include, without limitation, nitinol, stainless steel, and suitable nickel and titanium alloys, while flexible materials include, without limitation, ePTFE, fabric, etc. Other known materials that may be used for making the tube 102 (from FIG. 1) also may be used.

Towards the distal end 406 of the member 402, an expandable member may be coupled. The expandable member may include a stone enclosure, such as, e.g., a basket 410. In an embodiment, the lumen 408 of the member 402 may be in fluid communication with the interior of basket 410. For example, as shown, the proximal end 414 of basket 410 may be coupled to member 402 about the lumen 408. The proximal end 414 of the basket 410 may be permanently fixed to the distal end 406 of the member 402 or temporarily coupled such that it is selectively detachable. Permanent coupling can be provided using welding, adhesives, etc. while temporary coupling can be provided by use of screw threads, snap-fit arrangement, hook, wires, etc. The basket 410 may be configured to receive and encapsulate an enucleated piece tissue/stone or other unwanted material from within a patient's body.

The basket 410 may be made of flexible or rigid material(s) as required for intended applications. Such materials include synthetic plastics, polymers, or fiber. Alternately, the basket 410 can be made of a conducting material. In such cases, the outer or exposed surface/portion of the conducting material may be insulated to prevent accidental damage to neighboring or adjacent tissues/organs. The basket may further include webbing, mesh, screening, filaments, fabric, sheeting, or other such components and materials situated between one or more legs of the basket.

The shape of the basket 410 may be selected such that it facilitates easy insertion into the working channel 110. Accordingly, the basket 410 may be oval, parachute-like, conical, etc. in shape. Further, the edge of the basket 410 provided at the distal end 412 may be round, beveled, or include an otherwise atraumatic shape to prevent injury to the surrounding tissues. The wall of the basket 410 may be solid or net-like.

Basket 410 may be self-expanding or may be expanded via a suitable actuating mechanism. An actuating mechanism, like, e.g., control wires that pass through the lumen of member 402 (or may be embedded in walls of member 402) and controlled at the proximal end of member 402, can be used. For example, distal end 412 as well as the proximal end 414 may be collapsed while the member 402 is inserted into the working channel 110. Thereafter, the distal end 412 may self-expand or be expanded using the actuation mechanism. The distal end 412 may expand in the radial or longitudinal direction. In an embodiment, the distal end 412 may expand to attain a radial dimension larger than the proximal end 414 to facilitate capturing of tissue or other unwanted material. As shown in FIG. 4A, for example, the basket 410 may define a substantially conical shape when expanded.

In an embodiment, the diameter of the opening 416 of the basket 410 may correspond to the diameter of, e.g., a working channel 110. Alternately, if the basket 410 is made of collapsible material, the diameter of the opening 416 of the basket 410 may be lesser in the collapsed state or greater in the expanded state than the diameter of the working channel 110. For example, the basket 410 may be inserted in a collapsed configuration and once it extends out of the distal end 106 of the tube 102 adjacent to an intended site, it may self-expand or be expanded (using an actuating mechanism) to include any suitable diameter.

The basket 410 is used to capture the undesired material that needs to be removed from the body. After capturing tissue, for example, the distal end 412 may be collapsed using the actuation mechanism. In the collapsed configuration, the distal end 412 may be held firmly to ensure that the captured tissue remains inside the basket 410. For example, distal end 412 may be radially closed via a cinching process. The proximal end 414 may be expanded radially to facilitate evacuation of the tissue fragments. Alternately, however, proximal end 414 does not need to be expanded to effect evacuation of material disposed within basket 410. The diameter of the proximal end 414 on expansion may correspond to the diameter of the distal end 406 of the member 402. In embodiments where the proximal end 414 does not need to be expanded to evacuate contents from inside the basket 410, the diameter of the proximal end 414 in an unexpanded state may correspond to the diameter of the distal end 406 of the member 402.

In an alternate embodiment, a swivel mechanism (not shown) may be introduced at one of the proximal end 414 or distal end 406. The swivel mechanism may allow the basket 410 to swivel (e.g., articulate or pivot), allowing it to capture tissue, stones, or other unwanted material at a surgical site effectively. Any conventional swivel mechanism may be used without departing from the scope of the present disclosure. In addition, the member 402 may be selectively steerable to angle distal end 412 at desired surgical sites.

The basket 410 may be provided with one or more conducting elements, for example, wires 418. As shown in, e.g., FIG. 4A, wires 418 may extend radially away from distal end 406 of member 402. In addition, wires 418 may be arranged circumferentially about the distal end 406 of member 402. Further, a wire may be provided around the distal opening 416 of basket 410 to which wires 418 may be coupled. For example, each wire 418 may be coupled to the wire extending around the distal opening of basket 410. The wires 418 may be embedded in an inner surface of the basket 410. Alternately, the wires 418 may be coupled to the inner surface of the basket 410 using glue or adhesive. The wires 418 may be made of any conducting material including without limitation copper, aluminum, gold, or silver. In some embodiments, the internal surface of one or more wires 418 may be sharpened to a blade so as to cut through the tissue. In a further embodiment, wires 418 themselves may not be conductive. Instead, wires or legs 418 may serve to guide conductive elements to a conductive wire surrounding the distal opening 416. Further, in embodiments wherein the distal opening 416 is surrounded by a wire, a portion of the wire may not be conductive. For example, if the distal opening 416 is surrounded by a conductive wire, a portion of the conductive wire may be covered by an insulating covering.

The wires 418 and optionally the wire extending around the distal opening may be energized through wireless or wired connections. For a wireless connection, the proximal end 414 may include a receiver that may receive energy for example, radio frequency (RF), transmitted by a transmitter provided within, e.g., one of the ports 116. For a wired connection, conducting elements, e.g., a set of cables may run along the lumen 408 of the member 402 to connect the wires 418 to a power supply located at the proximal end 404. These conducting elements may run within the thickness of wall of the member 402 so as to not obstruct lumen 408. Alternatively, wires 418 may be connected to visualization devices 402 for power supply which in turn may be connected to an external power supply or a controller, either wirelessly or via cables. Once the wires 418 are energized, the captured tissue may be fragmented or otherwise reduce when basket 410 is collapsed on the tissue. In addition, once energized, the wire around the distal opening 416 may sever attached tissue (e.g., a pedunculated polyp) when the basket 416 is closed. The basket 410 may be opened and closed multiple times so as to repeatedly cut/dice/morcellate large tissue pieces into smaller fragments.

The outer surface of the basket 410 may be covered/coated with an insulating material and/or an anti-microbial coating to prevent injury to the surrounding tissues or inhibit any microbial growth on its surface, respectively. In addition, the outer surface of basket 410 may include any suitable coating such as, e.g., an anesthetic or any suitable therapeutic agent. The insulating material may provide either electrical or heat insulation or both. This may prevent damage to surrounding or adjacent tissues. The insulating material may be disposed in a web-like manner between adjacent and/or over wires 418. Exemplary insulating materials (preferably electrically non-conducting) include biocompatible plastics and other suitable insulating materials, such as polyurethane, pellethane, or the like. Further, the anti-microbial coating may include an antibacterial covering, which may contain an inorganic antibiotic agent, disposed in a polymeric matrix that may adhere to an antibiotic agent on the surface of the basket 410.

In some embodiments, a leading edge of the basket 410 may be sharpened to facilitate cutting tissue, for example. In one embodiment, the wire provided around distal opening 416 may be sharpened to facilitate providing the basket 410 with the sharpened leading edge. In addition, the wire around distal opening 416 may be configured to direct or focus energy at a particular location. Accordingly, the wire around distal opening 416 may include any suitable cross-section profile, such as, e.g., a profile including a pointed edge. The leading edge of the basket 410 may also include any suitable configuration known in the art. In one embodiment, for example, the leading edge of the basket may be flared out or include a beveled configuration. In another embodiment, the one or both of the internal or external surfaces of the leading edge may be substantially planar or flat.

Figure 4B:
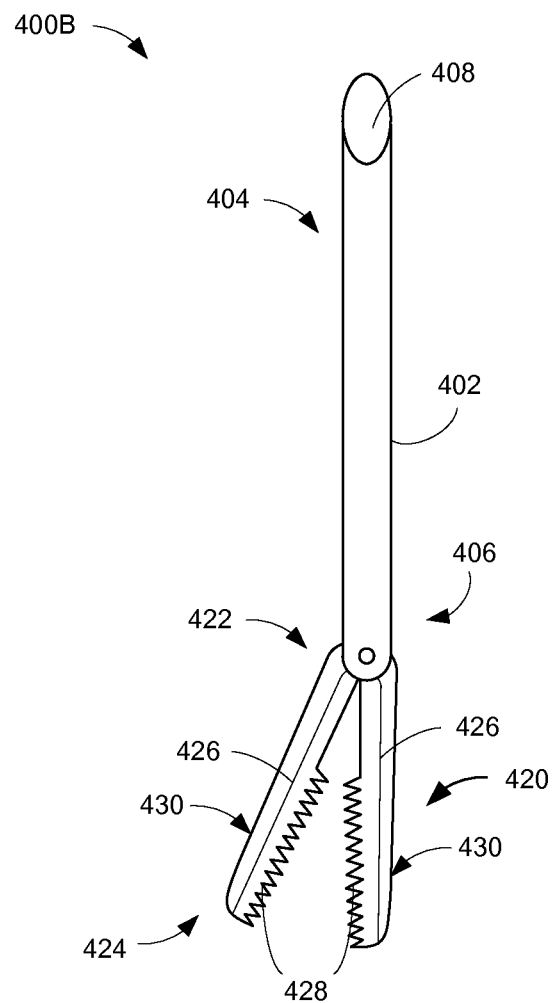

FIG. 4B depicts an alternate embodiment of a morcellating device 400B. The morcellating device 400B may include an elongate member 402 with a proximal end 404, distal end 406, and a lumen 408 extending between the two ends. The distal end 406 of the member 402 may be coupled to an expandable member, for example, an alligator forceps 420. As explained with respect to basket 410 in FIG. 4A, the alligator forceps 420 may be either permanently or removably coupled to the distal end 406. FIG. 4B depicts alligator forceps 420 being coupled to the distal end 406 of member 402 via a screw, which may allow one or both of jaws 428 to articulate relative to distal end 406. In the depicted embodiment, the member 402 may be rigid. The forceps 420 may include a distal end 424, a proximal end 422, and jaws 428 formed on inner surfaces of blades 430. Further, the inner surface of the blades 430 of the forceps 420 may be provided with one or more tangs 426 which may either be embedded in the walls of the forceps 420 at the time of manufacture or coupled using adhesives, glue, etc. Though a single tang is illustrated on each blade of the figure, multiple tangs may be used. Further, the forceps 420 may be made of conducting material, for example, aluminum, steel, and the like. Therefore, when the tangs 426 are energized, the jaws 428 and/or tangs 426 may be capable of cauterizing through tissue. The forceps 420 may include an insulating coating on an outer surface of each jaw 428, or any suitable portion thereof. The tangs 426 provided with the forceps 420 may be coupled to an energizing source either via a wired or wireless connection, as explained with regard to FIG. 4A.

The forceps 420 may be inserted in the channel 110 (shown in FIG. 1) when the jaws 428 are in a closed configuration. The forceps 420 may be manipulated to capture tissue (or other unwanted material) once extended out of the tube 102. The jaws 428 of the forceps 420 may be expanded or steered till the tissue may be captured partially or completely, as desired. The jaws 428 also may be energized to cut through pieces of captured tissue, as necessary. The forceps may be expanded or closed using an actuation mechanism provided at the proximal end 404. The tangs 418 attached to the forceps 420 may be energized as explained in FIG. 4A. Like basket 410, forceps 420 may be opened and closed multiple times until large tissue pieces have been sufficiently reduced.

Once the tissue is morcellated and reduced in size and/or hardness, the member 402 along with the forceps 420 (or basket 410 of FIG. 4A) may be withdrawn from the patient's body to remove tissue fragments. Alternatively, after the member 402 is removed, a vacuum device may be provided at the proximal end 404 to remove tissue fragments via suctioning. In some embodiments, after morcellation, pieces of tissue caught between the two jaws 428 may be suctioned/vacuumed out through the lumen 408. Although the depicted embodiment illustrates that jaws 428 may be connected to elongate member 402 in a manner that disposes a portion of one or both of jaws 428 in the path of lumen 408, those of ordinary skill in the art will understand that jaws 428 may be connected to elongate member 402 in a primarily external manner so as to avoid any portion of jaws 428 or their connection to elongate member 402 from blocking access to lumen 408. In a further embodiment, for example, only one of jaws 428 may be connected to an external portion of elongate member 402, and the other jaw 428 may be rotatably coupled to the first jaw 428. In further examples, the principles of the present disclosure contemplate including a separate tissue retrieval device (e.g., a suction tube) that may be used to retrieve tissue captured in between of jaws 428.

It will be appreciated that FIGS. 4A-4B are exemplary embodiments of the present disclosure. Other embodiments of expandable members include, without limitation, electrocautery scissors, coils, tweezers, etc. For example, the coil may unwind to open and wind to close. The windings of the coil may be energized to cut/slice through the tissue. In some embodiments, the coil may be wound to form a substantially cone-like configuration.

Figure 5A:
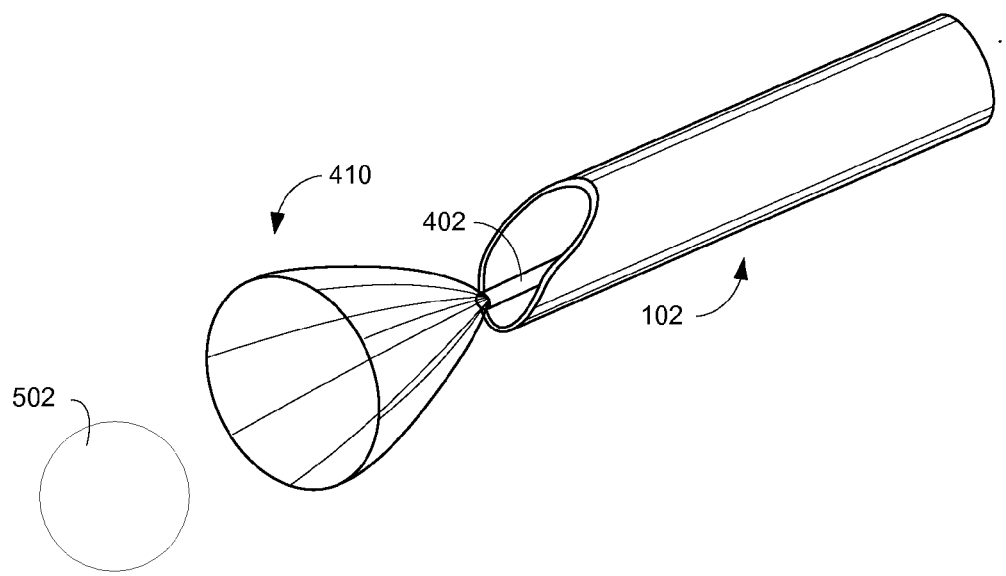
FIGS. 5A-5D are exemplary illustrations of the working of an assembly of the tube and the morcellating device, according to the present disclosure.

FIGS. 5A-5D are exemplary illustrations of the mechanism for morcellating using the morcellating device 400A. The morcellating device 400B may also work in a similar way. The morcellating device 400A may be provided in one of the working channels 110 of the device 100 of FIG. 1. In an embodiment, device 400A may be provided with the working channel 110 having a relatively larger diameter, as depicted in FIG. 3. Referring to FIG. 5A, the device 400A may be inserted into the working channel 110 through the proximal end 104 of the tube 102 such that the device 400A may extend out of the distal end 106 of tube 102 adjacent a desired location within a patient. In some embodiments, the desired location may be within a bladder. The basket 410 of the device 400A may be inserted into the working channel 110 in a collapsed configuration. Once the basket 410 extends out of the tube 102, the basket 410 may be expanded to achieve the illustrated configuration using the actuation mechanism described in FIG. 4A.

The movement of the device 400A may be controlled at the proximal end 104 of tube 102 manually or automatically. In some embodiments, the tube 102, for example, an endoscope or other suitable introduction sheath may first be inserted into the body followed by the device 400A. Alternately, the device 400A may be provided with the tube 102 and together the assembly may be inserted/advanced into a patient's body. Once placed inside the body, the basket 410 may be expanded to capture or encapsulate a tissue/stone 502 present at the desired location. The tissue may be, e.g., an already severed lobe of a prostate resulting from an enucleation procedure. As will be discussed below, collapsing the basket 410 about the tissue/stone 502 will at least serve the capture the tissue/stone 502. Alternatively, the tissue may be attached to the patient's body but targeted for separation from the patient's body. In this instance, collapsing the basket 410 about the tissue may sever the tissue from the patient's body as, e.g., a wire surrounding distal opening 416 cuts through the tissue.

Figure 5B:
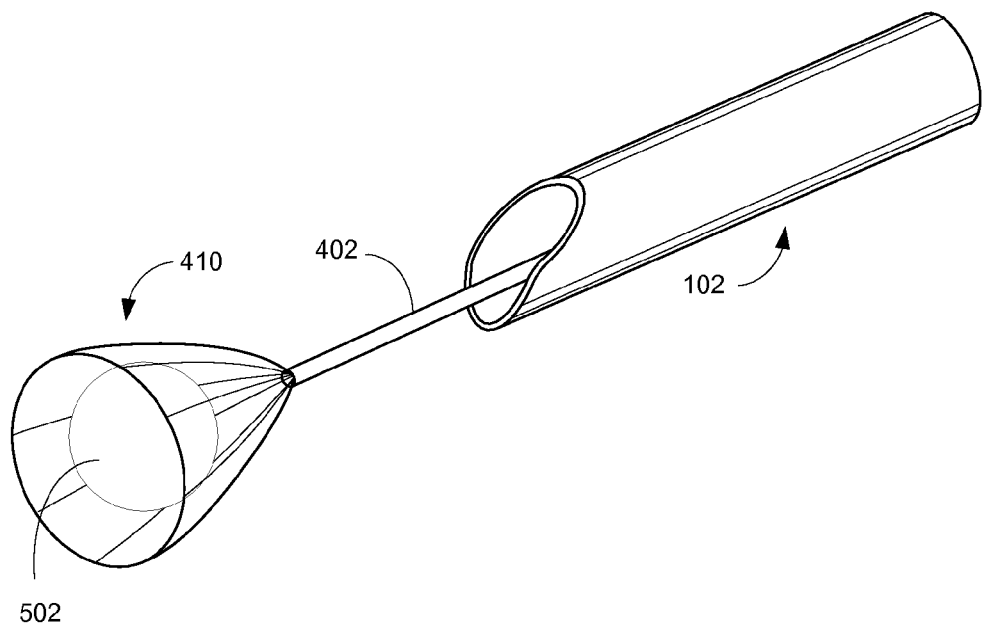

The member 402 may be moved to enable the basket 410 to capture and/or encapsulate the tissue 502 as shown in FIG. 5B. The member 402 may be steered using a steering mechanism attached at the proximal end 404 of the member 402. Exemplary steering mechanisms may include pull wires connected to a distal end of member 406 and extending up to the proximal end 404. For steering purposes, the pull wires may be controlled at the proximal end 404 automatically or manually. The light sources (shown in FIGS. 2-3) may aid in the movement or positioning of the member 402. The member 402 may be steered until the basket 410 may capture/encapsulate the tissue 502 partially or entirely. For example, if the tissue 502 is small, it may be captured in the basket 410 completely. However, if the tissue 502 is large, only portion of the tissue 502 may be captured in the basket 410 at a time. Alternately, in an embodiment, the size of basket 410 may be adjusted using control mechanism provided at the proximal end 404 to correspond to the size of the tissue 502.

Figure 5C:
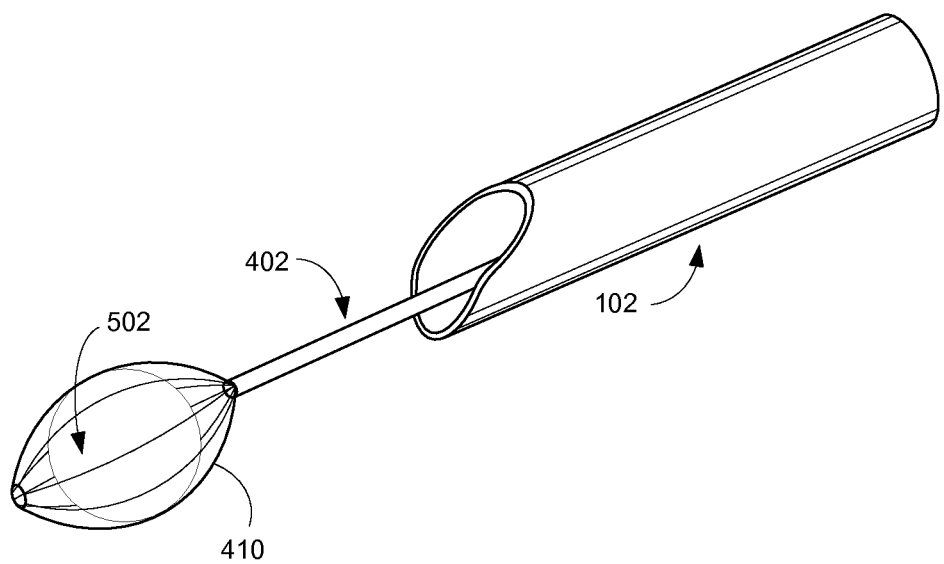

Once the tissue 502 is captured in the basket 410, the basket 410 may be closed to hold the tissue 502 in place. For example, as shown in FIG. 5C, a distal portion of basket 410 may be cinched closed. The distal end 412 of the basket 410 may be closed using, for example, an actuation mechanism, a control wire, etc. Subsequently, the wires 418 may be energized/heated using for example, RF energy, resistive heating, etc. For example, current may be passed through the wires 418 through conducting elements present in the member 402. The energized wires/tangs 418 may cut the tissue into smaller pieces, which could then be removed via, e.g., suction, vacuum, etc. through member 402. If, however, the suction force through member 402 is not sufficient to adequately remove tissue from basket 410, additional sources of vacuum or suction may be provided, such as, e.g., a discrete vacuum device.

Figure 5D:
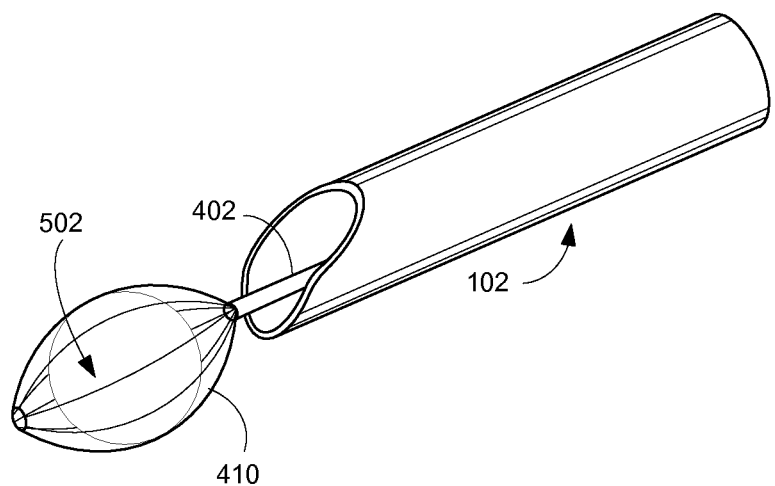

As shown in FIG. 5D, the tissue fragments may be removed by pulling the basket 410 towards the proximal end 404. Once the basket 410 is pulled out of the body, the tissue fragments may be removed. This procedure may be repeated until all of the fragments of the tissue are removed. Alternately, rather than removing and inserting the basket 410 each time from the tube 102, the member 402 may be coupled to a suction device at the proximal end 404. The proximal end 414 of the basket 410 may be expanded while keeping the distal end 412 of the basket 410 closed. Thereafter, using the suction mechanism, the fragments of the tissue may be suctioned out of the basket 410. As alluded to above, in some embodiments, the proximal end of basket 410 may not be expanded to effect suctioning of tissue pieces from within the basket 410.

It may thus be seen from the foregoing that owing to a wider working channel, larger tissue fragments can be removed without damaging the surrounding area/tissues. Further, using RF morcellation, the possibility of damaging the surrounding tissues is also eliminated and use of medical devices like irrigation devices, etc. is minimized.

Embodiments of the present disclosure may be used in any medical or non-medical procedure, including any medical procedure where removal of a body tissue, stone, or other unwanted material is required. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A medical device, the medical device comprising:
a tube including a proximal end, a distal end, and a lumen extending therebetween; and
an expandable member attached to the distal end of the tube, the expandable member including a plurality of conducting elements extending distally from the distal end of the tube, at least two of the plurality of conducting elements being joined together by a material extending therebetween to define a basket including an interior with a distal facing opening, the interior being in fluid communication with the lumen, each conductive element having a conductive inner surface facing towards the interior and a non-conductive outer surface facing away from the interior,
wherein the plurality of conducting elements are operable with a power source to selectively energize the plurality of conductive elements, and the basket is collapsible around a tissue to cut the tissue into multiple pieces with the conductive inner surfaces of the energized conductive elements so that at least one piece of the multiple pieces is removable from the interior with the lumen of the tube.

2. The medical device of claim 1, wherein the non-conductive outer surface of each of the plurality of conducting elements includes an insulating material extending distally from the distal end of the tube.

3. The medical device of claim 1, wherein the conductive inner surface of at least one of the plurality of conducting elements includes a sharpened blade.

4. The medical device of claim 1, wherein the non-conductive outer surface of at least one of the plurality of conducting elements includes an atraumatic configuration.

5. The medical device of claim 1, wherein the material forms a conductive ring, and the plurality of conductive elements are disposed about the ring to define the basket; further comprising an actuation mechanism configured to selectively move the conductive ring between an open configuration, in which the distal facing opening is radially expanded, and a closed configuration, in which the distal facing opening is radially closed.

6. The medical device of claim 1, wherein the expandable member includes a substantially conical shape when expanded.

7. The medical device of claim 6, wherein the plurality of conducting elements are disposed radially about the substantially conical shape.

8. The medical device of claim 1, wherein the expandable member is configured to transition between a collapsed configuration and an expanded configuration.

9. The medical device of claim 8, wherein the tube is configured to transition between a collapsed configuration and an expanded configuration.

10. A tissue retrieval system, the system comprising:
a sheath having a proximal end, a distal end, and a channel extending therebetween;
a morcellating device configured to be disposed within the channel, the device comprising:
a tube including a proximal end, a distal end, and a lumen extending therebetween along a longitudinal axis;
an expandable member attached to the distal end of the tube, the expandable member including a plurality of conducting elements extending distally from the distal end of the tube, at least two of the plurality of conductive elements being joined together by a material to define a basket including an interior with a distal facing opening, the interior being in fluid communication with the lumen, each of the plurality of conductive elements having a conductive inner surface facing toward the longitudinal axis and a non-conductive outer surface facing away from said axis,
wherein the plurality of conductive elements are operable with a power source to selectively energize the plurality of conductive elements, and the basket is collapsible around a tissue to cut the tissue into multiple pieces with the conductive inner surfaces of the energized conductive elements so that at least one piece of the multiple pieces is removable from the interior with the lumen of the tube.

11. The tissue retrieval system of claim 10,
wherein the channel comprises a plurality of channels, the morcellating device is disposed in one of the plurality of channels, and at least one of the remainder of the plurality of channels includes one of an illumination device and an imaging device, and
wherein one or both of the illumination device and the imaging device are removable from the sheath.

12. The tissue retrieval system of claim 10, further comprising a vacuum source coupled with the lumen.

13. The tissue retrieval system of claim 10, wherein an outer surface of each of the plurality of conducting elements is covered with an insulating material.

14. The tissue retrieval system of claim 10, wherein the material joining the plurality of conducting elements forms a conductive ring, the plurality of conducting elements are disposed about the conductive ring to define the basket, and the morcellating device comprises an actuation mechanism configured to selectively move the conductive ring between an open configuration, in which the distal facing opening is radially expanded, and a closed configuration, in which the distal facing opening is radially closed.

15. The tissue retrieval system of claim 14, wherein the basket is selectively closeable and expandable.

16. The tissue retrieval system of claim 14, wherein the power source selectively energizes the conductive ring.

17. A method of retrieving unwanted material from within a body, the method comprising:
advancing a morcellating device to a location adjacent the unwanted material within the body, the device comprising:
a tube including a proximal end, a distal end, and a lumen extending therebetween along a longitudinal axis; and
an expandable member attached to the distal end of the tube, the expandable member including a plurality of conducting elements extending distally from the distal end of the tube, at least two of the plurality of conductive elements being joined together by a material to define a basket including an interior with a distal facing opening, each of the plurality of conductive elements having an conductive inner surface facing toward the interior and a non-conductive outer surface facing away from the interior;
moving the tube to pass the unwanted material through the distal facing opening and entrap the unwanted material within the interior;
energizing the plurality of conducting elements with a power source;
collapsing the basket about the unwanted material to cut the unwanted material into multiple pieces with the conductive inner surfaces of the plurality of conductive elements; and withdrawing at least a portion of the unwanted material from the location within the body with the lumen of the tube.

18. The method of claim 17, wherein the unwanted material is a portion of tissue attached to the body, and the plurality of conductive elements are joined together by a conductive ring, further comprising:
   energizing the conductive ring with the power source; and
   collapsing the conductive ring to sever the portion of tissue from the body.

19. The method of claim 18, wherein:
   the morcellating device comprises an actuation mechanism configured to move the conductive ring between an open configuration, in which the distal facing opening is radially expanded, and a closed configuration, in which the distal facing opening is radially closed; and
   collapsing the conductive ring comprises operating the actuation mechanism to move the conductive ring between the open and closed configurations.

20. The medical device of claim 19, wherein collapsing the basket comprises engaging a portion of the of the basket with a portion of the sheath.

\* \* \* \* \*